(12) United States Patent
Shaffer et al.

(10) Patent No.: US 8,972,206 B2
(45) Date of Patent: Mar. 3, 2015

(54) PHASED ARRAY SCANNING INTO A CURVATURE

(75) Inventors: Chad Martin Shaffer, State College, PA (US); Peter Renzel, Münsterweg (DE); Jerome Poirier, Forges les Bains (FR); Michael Maria Berke, Cologne (DE); Douglas Paul Lutz, Lewistown, PA (US); Rai Mohan Dasarathan, Bangalore (IN); Anandamurugan S, Bangalore (IN)

(73) Assignee: General Electric Company, Schenectady, NY (US)

( * ) Notice: Subject to any disclaimer, the term of this patent is extended or adjusted under 35 U.S.C. 154(b) by 473 days.

(21) Appl. No.: 13/359,262

(22) Filed: Jan. 26, 2012

(65) Prior Publication Data

US 2013/0197822 A1    Aug. 1, 2013

(51) Int. Cl.
G01B 5/28    (2006.01)
G01N 9/24    (2006.01)

(52) U.S. Cl.
USPC .............................................. 702/39; 73/622

(58) Field of Classification Search
USPC ................. 702/39, 33–36, 108, 124, 127, 702/150–153, 155–159, 170–171, 189; 73/584, 588, 596–598, 600, 602, 607, 73/614–616, 618–622, 625, 627–629, 73/632–635, 637–638, 640–643, 73/645–646; 367/87, 99, 103–104, 367/118–120, 129
See application file for complete search history.

(56) References Cited

U.S. PATENT DOCUMENTS

| | | | |
|---|---|---|---|
| 5,497,662 A * | 3/1996 | Dykes | 73/634 |
| 6,789,427 B2 | 9/2004 | Batzinger et al. | |
| 7,694,569 B2 | 4/2010 | McGrath et al. | |
| 2004/0016299 A1 | 1/2004 | Glascock et al. | |
| 2008/0190205 A1 | 8/2008 | Messer et al. | |

* cited by examiner

*Primary Examiner* — Toan Le (57) ABSTRACT

A system for use in determining a location of a defect in an object is provided. The system includes an ultrasonic phased array configured to provide a sector scan of the object, a display, and a processor. The processor is programmed to provide a volume-corrected view of a sector of an ultrasonic inspection of the object on the display, wherein the object has a first surface defined by a first radius and a second surface defined by a second radius that is shorter than the first radius, receive gate parameters of a gate used to measure a location of a reflection of a beam emitted from the ultrasonic phased array, wherein the reflection is indicative of a defect on the first surface or the second surface, and calculate a location of the defect using the gate.

19 Claims, 7 Drawing Sheets

PHASED ARRAY SCANNING INTO A CURVATURE

BACKGROUND OF THE INVENTION

The field of the disclosure relates generally to an ultrasonic phased array, and more specifically to using an ultrasonic phased array for inspecting a curved surface.

Ultrasonic phased arrays are often used to generate and receive ultrasound. Instead of a single transducer and beam, phased arrays use multiple ultrasonic elements and electronic time delays to create beams via constructive and destructive interference. Phased array beams can be steered, scanned, swept, and/or focused electronically. Beam steering enables selected beam angles to be optimized ultrasonically by orienting them substantially perpendicularly to predicted discontinuities, such as, for example, a lack of fusion in automated welds. Beam steering, usually called sectorial or azimuthal scanning, can be used to map components at appropriate angles to optimize a probability of detection of discontinuities. Sectorial scanning is useful when a minimal footprint is possible. Electronic focusing enables a beam shape and size to be optimized at an expected defect location, as well as optimizing a probability of detection. Overall, the use of phased arrays permits optimizing discontinuity detection while minimizing testing time.

However, while phased arrays are often used to test an integrity of an object, such as a pipe, there is currently little or no ideal solution prevalent to perform circumferential scanning of objects having curved surfaces.

BRIEF DESCRIPTION OF THE INVENTION

In one aspect, a system for use in determining a location of a defect in an object is provided. The system includes an ultrasonic phased array configured to provide a sector scan of the object, a display, and a processor. The processor is programmed to provide a volume-corrected view of a sector of an ultrasonic inspection of the object on the display, wherein the object has a first surface defined by a first radius and a second surface defined by a second radius that is shorter than the first radius, receive gate parameters of a gate used to measure a location of a reflection of a beam emitted from the ultrasonic phased array, wherein the reflection is indicative of a defect on the first surface or the second surface, and calculate a location of the defect using the gate.

In another aspect, a method for determining a location of a defect in an object is provided. The method includes providing a volume-corrected view of a sector of an ultrasonic inspection of the object, wherein the object has a first surface defined by a first radius and a second surface defined by a second radius that is shorter than the first radius, receiving parameters of a gate used to measure a location of a reflection of a beam emitted from the ultrasonic phased array, wherein the reflection is indicative of a defect on the first surface or the second surface, and calculating a location of the defect using the gate.

In yet another aspect, one or more computer storage media embodying computer-executable instructions stored thereon are provided. The instructions include providing a volume-corrected view of a sector of an ultrasonic inspection of an object, wherein the object has a first surface defined by a first radius and a second surface defined by a second radius that is shorter than the first radius, receiving parameters of the gate used to measure a location of a reflection of a beam emitted from an ultrasonic phased array, wherein the reflection is indicative of a defect on the first surface or the second surface, and wherein the beam includes a first leg and a second leg between the gate start and the gate end, and calculating a location of the defect using the gate.

BRIEF DESCRIPTION OF THE DRAWINGS

The present disclosure is described in detail below with reference to the attached drawing figures.

Corresponding reference characters indicate corresponding parts throughout the drawings bound.

DETAILED DESCRIPTION OF THE INVENTION

In the field of ultrasonic inspections of objects having curved surfaces, use of angle-corrected views or uncorrected views provide a user with a location of a defect in an object. However, a visual depiction of a location of the defect generally starts to deviate from an actual location after a first leg of a beam during the inspection.

Figure 1:
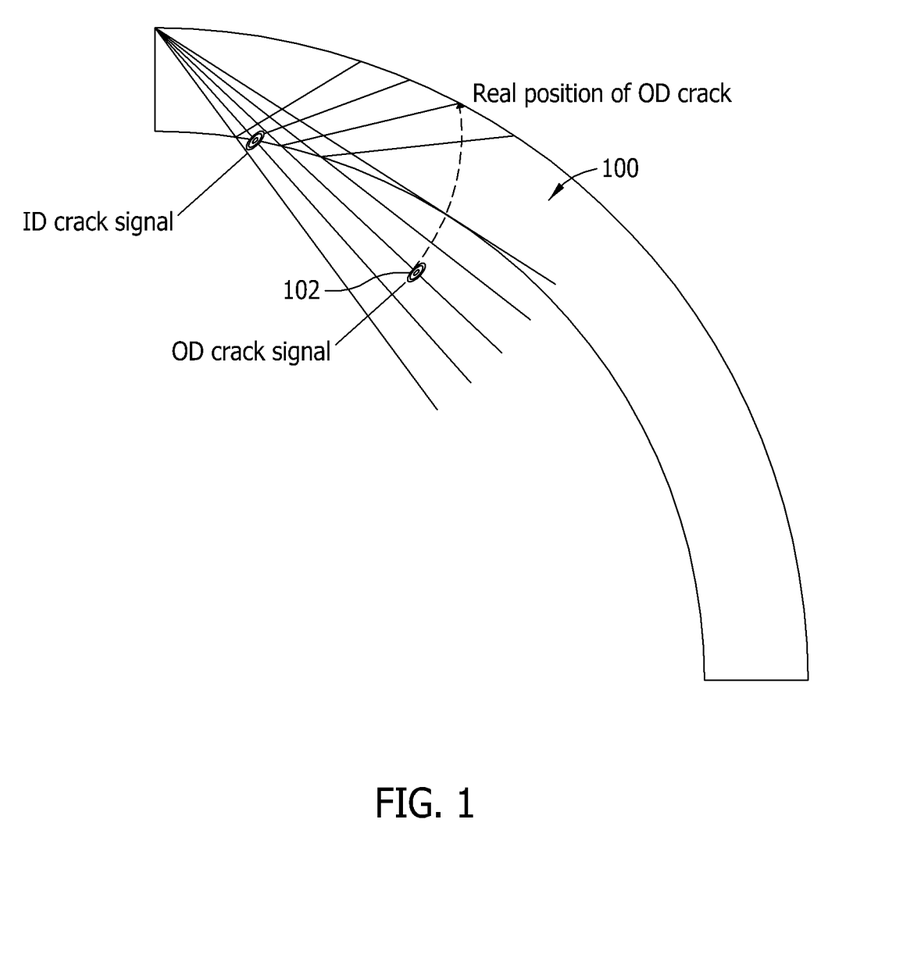
FIG. 1 provides an angle-corrected view of an exemplary ultrasonic inspection.

As described herein, a "leg" in ultrasonic inspection refers to a segment sound travels from one surface to another (e.g., outside diameter to inside diameter) in an object. For example, FIG. 1 provides an angle-corrected view of an ultrasonic inspection of a pipe 100. With an angle-correct view, all indications in a second leg or higher can visually not be related to their real position in a wall of pipe 100. Thus, it is difficult for a user to accurately identify an actual location of defect 102 because, due to the techniques used to calculate a location of a defect beyond the first leg of a beam, defect 102 is not shown to the user in its actual location on an outer diameter of pipe 100.

The present disclosure enables a location of a defect to be shown at an actual position with respect to an object having a curved surface. Further, the present disclosure enables a location of a defect to be calculated independently of a leg number of a beam the defect falls on.

One of ordinary skill in the art guided by the teachings herein will appreciate that while embodiments of the disclosure are illustrated and described herein with reference to using an ultrasonic phased array to scan an object with a curved surface (e.g., a pipe), aspects of the disclosure are operable with any system that performs the functionality illustrated and described herein, or its equivalent.

An exemplary technical effect of the methods and systems described herein includes at least one of (a) providing a volume-corrected view of a sector of an ultrasonic inspection of the object, wherein the object has a first surface defined by a first radius and a second surface defined by a second radius that is shorter than the first radius; (b) receiving parameters of a gate used to measure a location of a reflection of a beam emitted from the ultrasonic phased array, wherein the reflection is indicative of a defect on the first surface or the second surface; and (c) calculating a location of the defect using the gate.

Figure 2:
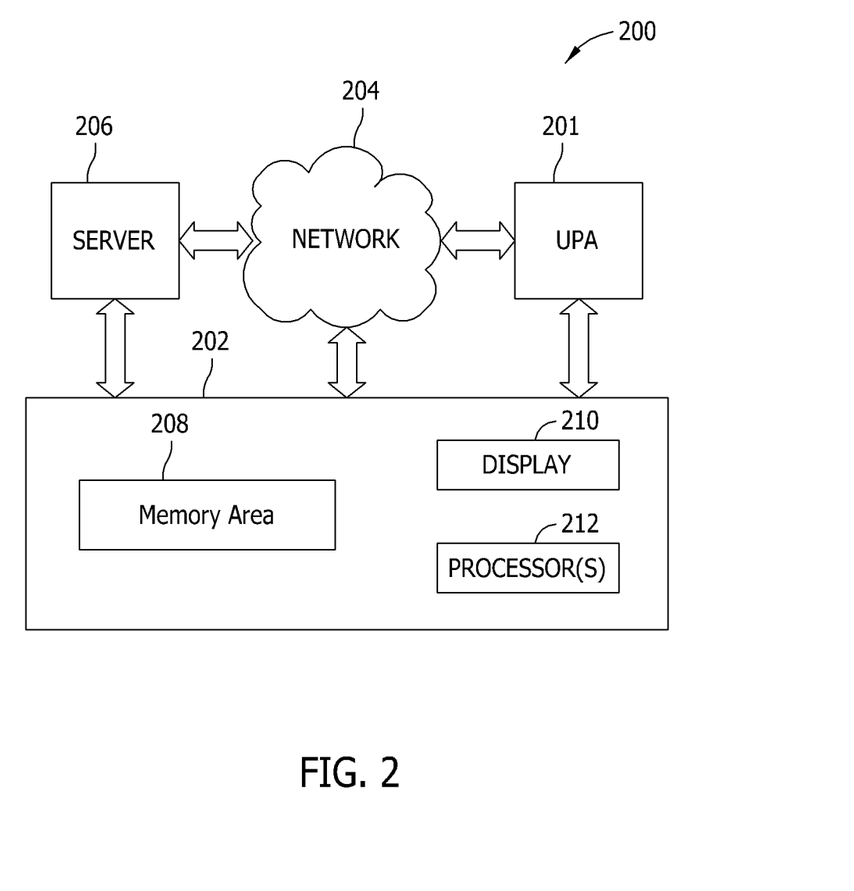
FIG. 2 is a block diagram of an exemplary system for use in determining a location of a defect in an object with a curved surface.

Referring now to FIG. 2, a block diagram of an exemplary system 200 that may be used to determine a location of a defect in an object is provided. System 200 is but one example of a suitable system and is not intended to suggest any limitation as to the scope of use or functionality of the present disclosure. Further, system 200 should not be interpreted as having any dependency or requirement relating to any one or combination of components illustrated herein.

System 200 includes an ultrasonic phased array (UPA) 201, a computing device 202, a network 204, and a server 206. While, one of ordinary skill in the art guided by the teachings herein will appreciate that aspects of the disclosure are operable with any ultrasonic phased array that performs the functionality illustrated and described herein, or its equivalent, UPA 201 may be a portable phased array unit with manual, semi-automated, and/or automated capabilities. In one embodiment, UPA 201 is a 16/128 unit (16 multiplexed pulsers with 128 channels), with up to 256 focal laws (individual beam pulses). UPA 201 may be able perform electronic and sectorial scans, be fully digital, perform encoded scans, perform full waveform data at multiple angles/positions, as well as display combined scans giving facilitate increased imaging capability. UPA 201 may also include built-in reporting capability (using pasted in scans) and have internal procedure capability. In one embodiment, UPA 201 may include a "probe recognition" function, where an array is automatically detected and characterized when connected, thus eliminating programming array parameters.

Further, while some embodiments of the disclosure are illustrated and described herein with reference to server 206 being a server computing device, embodiments of the disclosure are operable with netbooks, desktop computing devices, laptop computers, and other computing devices. In such embodiments, data may be stored by a cloud service and accessible by any computing device implementing functionality of the disclosure.

In the exemplary embodiment, an exemplary block diagram illustrates computing device 202 including a memory area 208 for storing computer-executable instructions for determining a location of a defect in an object with a curved surface. Computing device 202 further includes a display 210 and at least one processor 212. Display 210 may be, for example, a capacitive touch screen display that is integrated into computing device 202 or external to computing device 202. User input functionality is provided in display 210 which acts as a user input selection device as well as a means to provide a user with a predictive dose-volume relationship. In embodiments, display 210 is configured to be responsive to a user pressing contact on display 210 to selectively perform functionality. Thus, a user can operate desired troubleshooting functions available with computing device 202 by contacting a surface of display 210 as well as other functions provided herein.

In one embodiment, the computer-executable instructions for determining a location of a defect in an object with a curved surface are stored and executed from a memory area remote from computing device 202. For example, instructions may be stored in a cloud service, a database, or other memory area accessible by computing device 202. Such embodiments reduce the computational and storage burden on computing device 202.

Processor 212 executes computer-executable instructions for implementing aspects of the disclosure. In one embodiment, processor 212 is transformed into a special purpose microprocessor by executing computer-executable instructions or by otherwise being programmed. In general, processor 212 may be programmed with instructions/operations illustrated and next described in FIG. 3.

Figure 3:
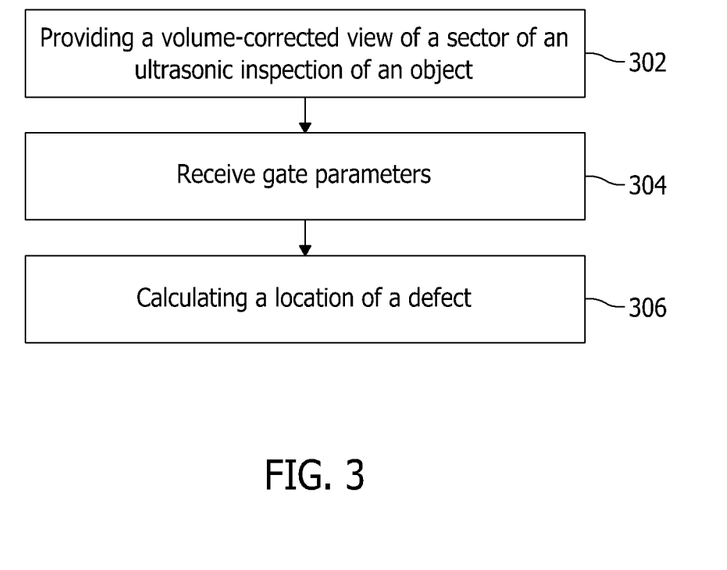
FIG. 3 is a flow chart illustrating an exemplary process for determining a location of a defect in an object with a curved surface.
Figure 4:
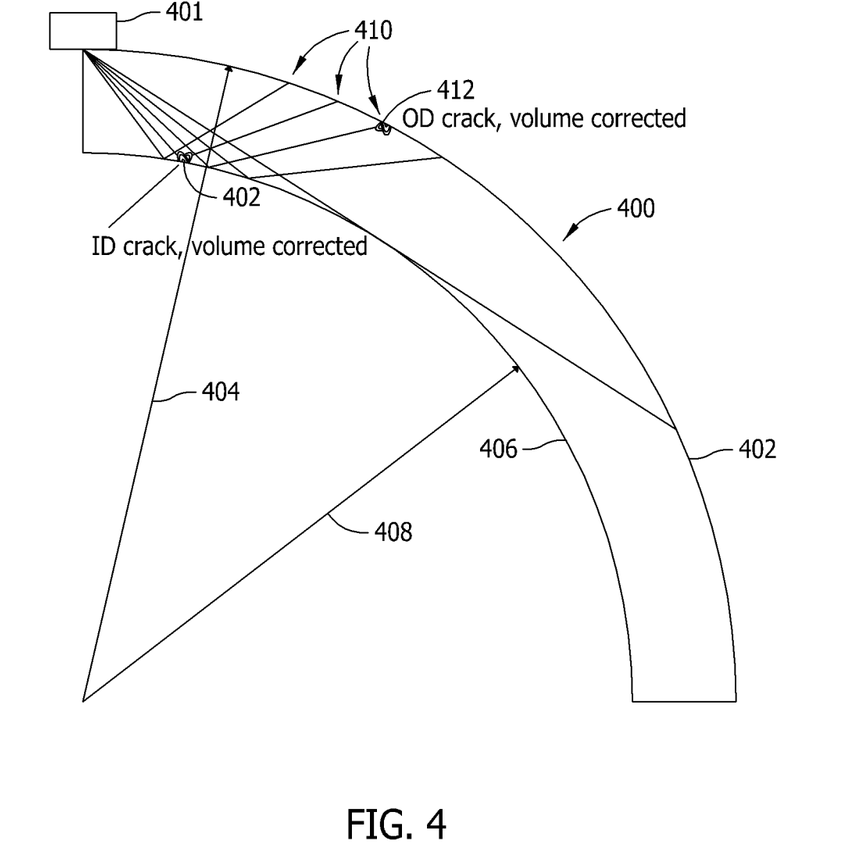
FIG. 4 provides a volume-corrected view of an exemplary sector scan.

Referring now to FIG. 3, a flow chart illustrates an exemplary process for determining a location of a defect in an object with a curved surface. Initially, a volume-corrected view of a sector of an ultrasonic inspection of the object is provided 302. For example, with reference now to FIG. 4, a volume-corrected view of an exemplary sector scan of a pipe 400 is illustrated. In the exemplary embodiment, pipe 400 includes a first surface 402 defined by a first radius 404, and a second surface 406 defined by a second radius 408 that is less than first radius 404. Thus, beams 410 emitted from an ultrasonic phased array (UPA) 401 are in their accurate positions as they reflect off of second surface 406. Further, defects, such as defect 412 are shown at their accurate positions with respect to pipe 400, independent of leg beams 410.

Gate parameters are then received 304. Each gate is a functional tool used to measure a size (e.g., an amplitude) and a location (e.g., a time-of-flight) of a reflection of a beam from, for example, UPA 201 in FIG. 2. In one embodiment, the gate parameters are variably selected by a user. For example, with reference to FIG. 5, a volume-corrected image 502 of a sector of a pipe 500 (e.g., a ¼ circumference of pipe 500) is displayed to a user with a graphic overlay of a sector gate 508. Displaying volume-corrected image 502 with graphic overlay 504 to a user provides a user with a sense of a location of a defect (e.g., defect 506) as well as a user-friendly means to define a gate width 516 for sector gate 508. Moreover, such a display enables a user to variably position sector gate 508 such that defect 506 is within sector gate 508.

Figure 5:
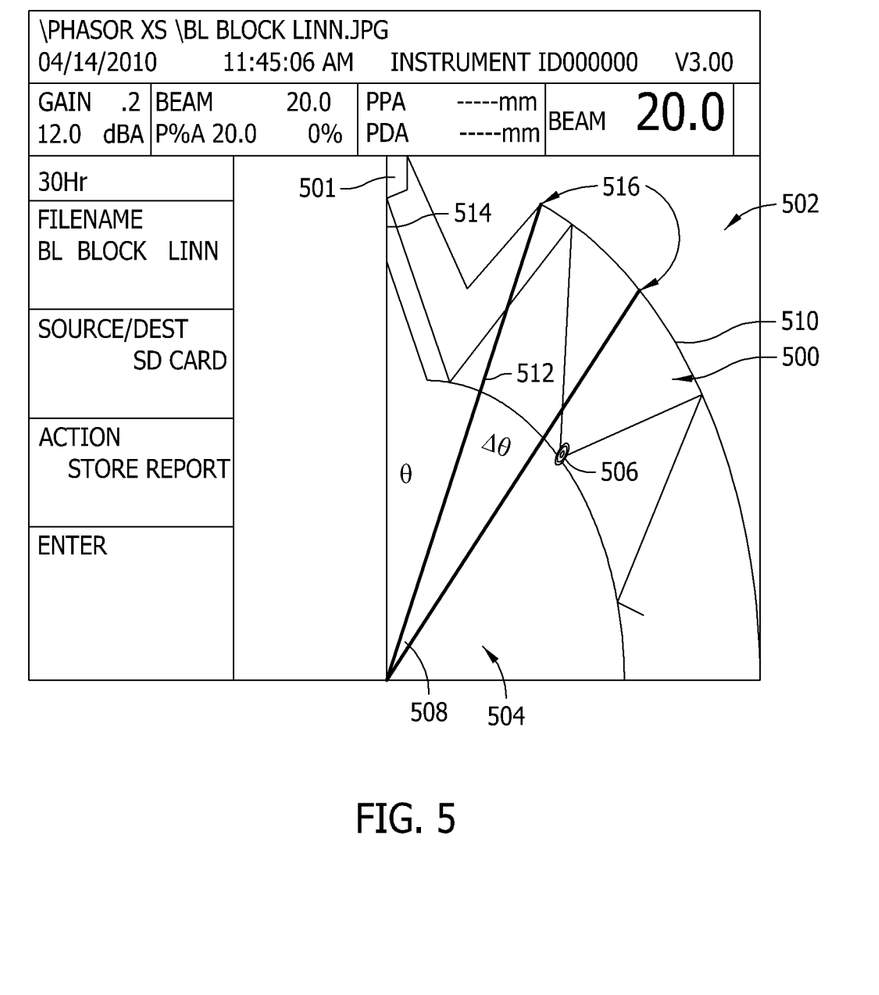
FIG. 5 provides a volume-corrected view of an exemplary sector scan with a graphic overlay of a sector gate.

For example, in the exemplary embodiment, volume-corrected image 502, with graphic overlay 504, enables a user to enter a gate range for sector gate 508 as well as define a gate start 512 (e.g., enables a user to position sector gate 508 such that defect 506 is within sector gate 508 optimizing the positioning of sector gate 508). Once a user has specified a width 516 of sector gate 508 along a surface 510 of pipe 500, a sector gate theta (θ) and delta-theta (Δθ) can automatically be calculated from the inputs. For example, in the exemplary embodiment, a start of sector gate 508 is defined by an angle, theta (θ), and a width of sector gate 508 is defined by a second angle, delta-theta (Δθ). As such, a start of sector gate 508 is measured by a distance along surface 510 from origin line 514 to a desired start of sector gate 508, for example, at gate start 512. Further, because gate start 512 is measured from origin line 514 along a surface 510 of pipe 500, the user may specify gate start 512 as the distance along surface 510 from origin line 514 to a desired start of a gate range for sector gate 508.

In one embodiment, rather than enabling a user to select sector gate parameters (e.g., a start of a sector gate and a width of the sector gate), system 200 enables an auto sector gate (ASG) to automatically define gate parameters and an auto beam curser (ABC) to automatically determine a gate position, without user intervention.

Figure 6:
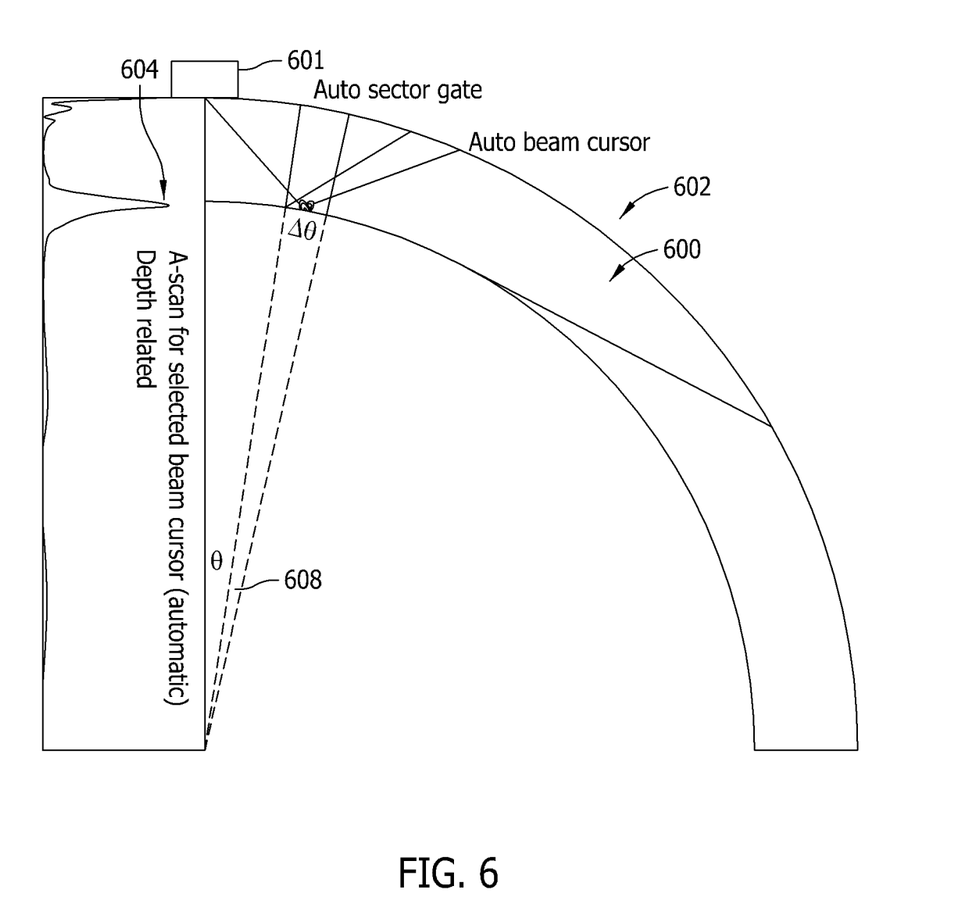
FIG. 6 provides a volume-corrected view of an exemplary sector scan used in conjunction with an auto sector gate and an auto beam curser.

With reference now to FIG. 6, an exemplary volume-corrected image 602 of pipe 600 is provided. In one embodiment, the ABC increases automatically and stops at a maximum signal amplitude, as shown in A-scan at 604. Further, by moving UPA 601, the ABC automatically maintains a maximum echo indication visible because the ABC automatically follows a maximum amplitude. In addtion, similar to a user-defined sector gate, a start of a sector gate 608 defined by an ASG is defined by an angle, theta (θ) and a width of sector gate 608 is defined by a second angle, delta-theta (Δθ). The starting angle, theta (θ) of the ASG automatically increases (from 0) to bring it to a position where a first maximum defect echo falls into a middle of sector gate 608. Thus, with sector gate 608 in position, all correct defect-related readings can be displayed.

In one embodiment, the ASG defines gate parameters of a reference object prior to defining gate parameters of sector gate 608. Enabling the ASG to define gate parameters of a reference object (e.g., a model of pipe 600) enables the ASG to test gate parameters prior to defining the parameters for sector gate 608, thus, optimizing the parameters used to define sector gate 608.

Therefore, the ABC enables a display of a maximum reference amplitude while the ASG follows a maximum indication. As such, while moving UPA 601 in order to scan a defect using multiple angles, a beam cursor and sector gate 608 automatically follow a maximum indication. In one embodiment, if further echoes need to be evaluated, a function may increase a beam number to stop at a next echo, and the ASG will thus follow automatically.

Figure 7:
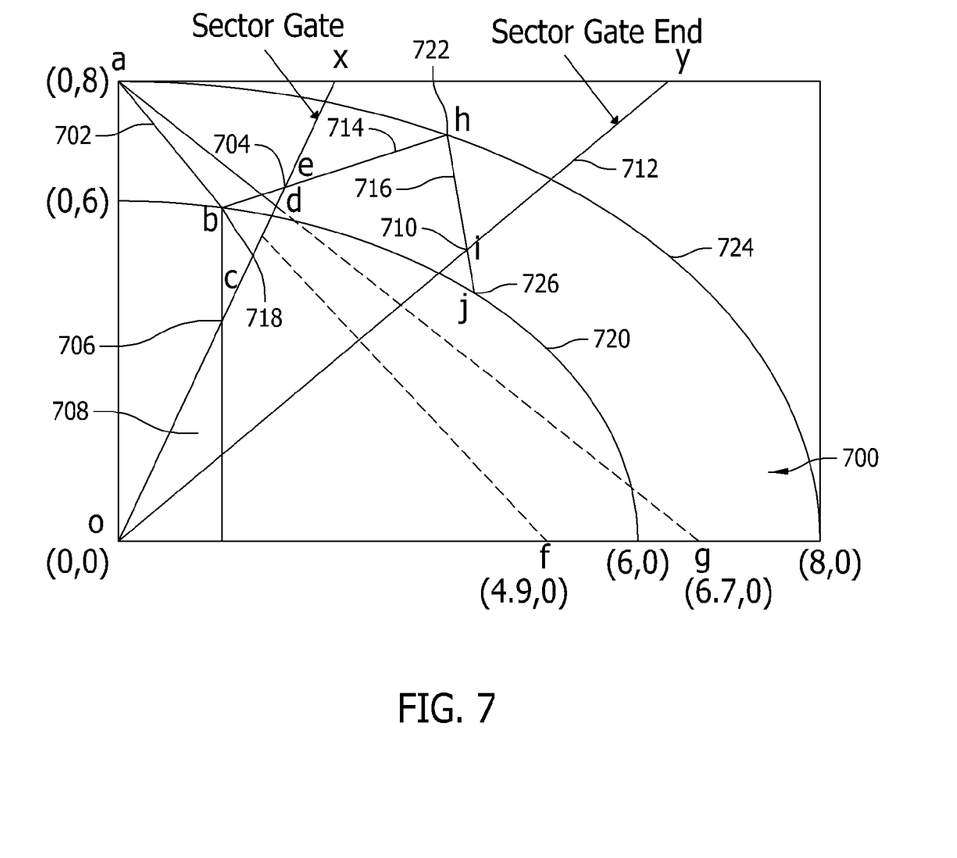
FIG. 7 provides a volume-corrected view of an exemplary sector scan.

With reference back to FIG. 3, a location of a defect is calculated 306. To calculate a location of a defect, a sound path distance of an ultrasonic beam angle to a start and an end of a sector gate region is calculated for each ultrasonic beam angle in a sector scan. For example, with reference now to FIG. 7, a volume-corrected view of a sector scan of a pipe 700 is provided. In one embodiment, a point 704 where a beam 702 intersects a start 706 of a sector gate 708 and a point 710 where beam 702 intersects an end 712 of sector gate 708 is identified, and a distance of beam 702 from gate start intersection point 704 to gate end intersection point 710 is calculated. However, as shown in FIG. 7, beam 702 includes a plurality of legs (e.g., first leg 714 and second leg 716) between gate start 706 and gate end 712. For example, first leg 714 is a portion of beam 702 from a point 718 where beam 702 reflects off of a surface 720 of pipe 700 to a point 722 where beam 702 reflects off of a surface 724 of pipe 700, and second leg 716 is a portion of beam 702 from point 722 to a point 726 where beam 702 reflects off of a surface 720 of pipe 700.

To calculate a distance of beam 702, a location and distance of each leg within beam 702 is determined. In one embodiment, Cartesian coordinates of first leg 714 and second leg 716 along beam 702 are found and (x, y) coordinates of first leg 714 and second leg 716 are identified. For example, for point 704, a line-to-line intersection method may be used to identify a point of intersection of first leg 714 of beam 702 and gate start 706. A gate start is thus defined by the sum of each complete leg length of beam 702 before gate start 706 plus a partial leg length (if any) to gate start 706, and a gate end is defined by the sum of each complete leg length before gate end 712 plus a partial leg length (if any) to gate end 712. Thereafter, a gate width can be determined by subtracting the calculated gate start from the calculated gate end. A location of a defect is then calculated based on, for example, the calculated gate start, gate end, and gate width.

Exemplary Operating Environment

A computer or computing device such as computing device 202 and server 206 described herein have one or more processors or processing units, system memory, and some form of computer readable media. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Combinations of any of the above are also included within the scope of computer readable media.

The computer may operate in a networked environment using logical connections to one or more remote computers, such as a remote computer. Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

The present disclosure enables a location of a defect to be shown at an actual position with respect to an object having a curved surface. Further, the present disclosure enables a location of a defect to be calculated independently of a leg number of a beam the defect falls on.

Aspects of the disclosure transform a general-purpose computer into a special-purpose computing device when configured to execute the instructions described herein.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A system for use in determining a location of a defect in an object, the system comprising:
    an ultrasonic phased array configured to provide a sector scan of the object;
    a display; and
    a processor programmed to:
    provide a volume-corrected view of a sector of an ultrasonic inspection of the object on the display, wherein the object has a first surface defined by a first radius and a second surface defined by a second radius that is shorter than the first radius;
    receive gate parameters of a gate, comprising a gate start and a gate end, used to measure a location of a reflection, wherein the reflection is indicative of a defect on the first surface or the second surface; and
    calculate a location of the defect using the gate, by calculating a sound path distance of an ultrasonic beam angle of an ultrasonic beam to the gate start and the gate end for each ultrasonic beam angle in a sector scan; wherein the ultrasonic beam reflects off of the first surface and the second surface.

2. The system of claim 1, wherein the processor is further programmed to position the gate such that the defect on the object is within the gate.

3. The system of claim 2, wherein the processor is further programmed to receive a distance from an origin line of the sector scan to one of a start of the gate or a center of the gate.

4. The system of claim 1, wherein to calculate a location of the defect in the object, the processor is further programmed to:
    identify a point where the beam intersects the gate start and a point where the beam intersects the gate end;
    calculate a distance of the beam from the gate start intersection point to the gate end intersection point; and
    calculate a location of the defect based on the calculated distance of the beam from the gate start intersection point to the gate end intersection point.

5. The system of claim 4, wherein the processor is further programmed to receive gate parameters of a gate used to measure a location of a reflection of a beam that includes a first leg and a second leg between the gate start and the gate end.

6. The system of claim 1, wherein providing a volume-corrected view of a sector of an ultrasonic inspection of the object on the display comprises a graphic overlay of a sector gate that enables a user to select the gate parameters.

7. The system of claim 6, wherein the processor is further programmed to receive a selection of the position of the gate from a user such that the position of the defect of the object is within the gate.

8. The system of claim 1, wherein the processor is further programmed to enable an auto beam curser to position the gate such that the defect of the object is within the gate.

9. The system of claim 1, wherein the processor is further programmed to enable an auto sector gate to automatically select the gate parameters.

10. A method for determining a location of a defect in an object, the method comprising:
    providing a volume-corrected view of a sector of an ultrasonic inspection of the object, wherein the object has a first surface defined by a first radius and a second surface defined by a second radius that is shorter than the first radius;
    receiving parameters of a gate used to measure a location of a reflection of a beam emitted from the ultrasonic phased array, wherein the reflection is indicative of a defect on the first surface or the second surface; and
    calculating a location of the defect using the gate, wherein the calculation comprises:
        identifying a point where the beam intersects a gate start and a point where the beam intersects a gate end;
        calculating a distance of the beam from the gate start intersection point to the gate end intersection point; and
        calculating a location of the defect based on the calculated distance.

11. The method of claim 10, further comprising positioning the gate such that the defect on the object is within the gate.

12. The method of claim 11, wherein receiving parameters of a gate further comprises receiving parameters of a gate that are representative of a distance from an origin line of the sector scan to a start of the gate or a center of the gate.

13. The method of claim 10, further comprising receiving parameters of a gate used to measure a location of a reflection of a beam that includes a first leg and a second leg between the gate start and the gate end.

14. The method of claim 13, further comprising receiving, from the user, a selection of a position of the gate such that the position of the defect on the object is within the gate.

15. The method of claim 14, further comprising enabling an auto beam curser to position the gate such that the defect on the object is within the gate.

16. The method of claim 10, wherein providing a volume-corrected view of a sector of an ultrasonic inspection of the object further comprises providing a graphic overlay of a sector gate that enables a user to select the gate parameters.

17. The method of claim 10, further comprising enabling an auto sector gate to automatically select the gate parameters.

18. The method of claim 10, wherein the defect is determined to be on the first surface when a beam angle occurs on the first surface in the sector gate when the sector gate is positioned such that a first maximum echo falls in the middle of the sector gate and the defect is determined to be on the second surface when a beam angle occurs on the second surface in the sector gate when the sector gate is positioned such that a second maximum echo falls in the middle of the sector gate.

19. One or more non-transitory computer storage media embodying computer-executable instructions stored thereon, the instructions comprising the steps of:

providing a volume-corrected view of a sector of an ultrasonic inspection of an object, wherein the object has a first surface defined by a first radius and a second surface defined by a second radius that is shorter than the first radius;

receiving parameters of the gate used to measure a location of a reflection of a beam emitted from an ultrasonic phased array, wherein the reflection is indicative of a defect on the first surface when there is a defect on the first surface and indicative of a defect on the second surface when there is a defect on the second surface, and wherein the beam includes a first leg and a second leg between the gate start and the gate end; and calculating a location of the defect using the gate, by:

identifying a point where the beam intersects a gate start and a point where the beam intersects a gate end;

calculating a distance of the beam from the gate start intersection point to the gate end intersection point; and calculating a location of the defect based on the calculated distance.

* * * * *

UNITED STATES PATENT AND TRADEMARK OFFICE
CERTIFICATE OF CORRECTION

PATENT NO. : 8,972,206 B2  
APPLICATION NO. : 13/359262  
DATED : March 3, 2015  
INVENTOR(S) : Shaffer et al.

Page 1 of 1

It is certified that error appears in the above-identified patent and that said Letters Patent is hereby corrected as shown below:

On the Title Page, Item (75), under "Inventors", in Column 1, Line 6, delete "Rai Mohan Dasarathan," and insert -- Raj Mohan Dasarathan, --, therefor.

Signed and Sealed this  
Fifth Day of January, 2016

Michelle K. Lee  
*Director of the United States Patent and Trademark Office*